United States Patent [19]

Ito et al.

[11] Patent Number: 4,992,438

[45] Date of Patent: * Feb. 12, 1991

[54] PYRIMIDINE DERIVATIVES, PROCESS FOR PREPARING THE SAME AND AGRICULTURAL OR HORTICULTURAL FUNGICIDAL COMPOSITION CONTAINING THE SAME

[75] Inventors: Shigekazu Ito; Katsumi Masuda, both of Shizuoka; Shoji Kasano, Hamamatsu; Toshihiro Nagata, Shizuoka; Yoshiyuki Kojima, Kakegawa; Nobumitsu Sawai; Shinichiro Maeno, both of Shizuoka, all of Japan

[73] Assignees: Kumiai Chemical Industry Co., Ltd.; Ihara Chemical Industry Co., Ltd., both of Tokyo, Japan

[ * ] Notice: The portion of the term of this patent subsequent to Mar. 21, 2006 has been disclaimed.

[21] Appl. No.: 512,901

[22] Filed: Apr. 20, 1990

Related U.S. Application Data

[63] Continuation of Ser. No. 127,426, Dec. 2, 1987, abandoned.

[30] Foreign Application Priority Data

Dec. 3, 1986 [JP] Japan ................. 61-288247

[51] Int. Cl.$^5$ ................. A61K 31/505; C07D 239/42; C07D 239/46; A01N 43/54
[52] U.S. Cl. ................. 514/275; 514/272; 544/321; 544/330; 544/332
[58] Field of Search ................. 544/321, 330, 332; 514/272, 275

[56] References Cited

U.S. PATENT DOCUMENTS

| | | | |
|---|---|---|---|
| 3,974,276 | 8/1976 | Barlow et al. | 514/272 |
| 3,980,781 | 9/1976 | Snell et al. | 544/321 |
| 4,082,535 | 4/1978 | Hoegerle et al. | 544/330 |
| 4,092,150 | 5/1978 | Treves | 544/321 |
| 4,248,618 | 2/1981 | Serban et al. | 71/92 |
| 4,248,619 | 2/1981 | Serban et al. | 71/92 |
| 4,814,338 | 3/1989 | Ito et al. | 544/330 |

FOREIGN PATENT DOCUMENTS

| | | |
|---|---|---|
| 0126254 | 11/1984 | European Pat. Off. . |
| 0172786 | 9/1986 | European Pat. Off. . |
| 1800708 | 4/1969 | Fed. Rep. of Germany ...... 544/330 |
| 1245085 | 9/1971 | Fed. Rep. of Germany . |
| 151404 | 10/1981 | Fed. Rep. of Germany . |

OTHER PUBLICATIONS

Franke et al., CA, 96-157395n, (1982), "Fungicidal Compositions Containing Pyrimidines".
Serban et al., CA 94-65716y, (1981).
Ito et al., CA 104-168491a, (1986).
Evers et al., CA 104-148917r, (1986).

Primary Examiner—Cecilia Shen
Attorney, Agent, or Firm—Nixon & Vanderhye

[57] ABSTRACT

Disclosed are pyrimidine derivatives represented by general formula (I)

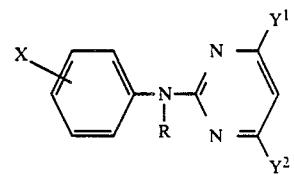

wherein X represents a hydrogen atom, a halogen atom, an alkyl group, an alkoxy group, a haloalkyl group or a cyano group; $Y^1$ represents an alkyl group, a cyanoalkyl group, an alkoxy group, an alkenyl group substituted with a hydroxy group and a halogen atom, an alkynyl group which may be substituted with a hydroxy group, a methylamino group, an alkoxyalkyloxy group, an alkylthioalkyl group or a group of the formula —CH$_2$OR$^1$ where R$^1$ represents a hydrogen atom, an alkyl group, an alkenyl group or an alkynyl group; $Y^2$ represents a halogen atom, an alkyl group or a haloalkyl group; R represents a hydrogen atom, an alkyl group, a nitroso group, an alkoxyalkyl group, an alkoxyalkyloxyalkyl group, an alkenyl group, an alkynyl group, a formyl group or an alkylthioalkyl group, with the proviso that (a) when $Y^1$ represents an alkynyl grop or when $Y^1$ represents an alkoxy group and $Y^2$ represents a halogen atom or an alkyl group, X and R are not a hydrogen atom simultaneously, (b) when $Y^1$ and $Y^2$ each represents an alkyl group, R is not a hydrogen atom, or (c) when $Y^1$ represents an alkyl group and $Y^2$ represents a halogen atom, X and R are not a hydrogen atom simultaneously or X is not a halogen atom nor an alkyl group. Also, agricultural or horticultural compositions containing the pyrimidine derivatives as active ingredient are disclosed, which show high controlling activities for cucumber gray mold (*Botrytis cinerea*), cucumber downey mildew (*Pseudoperonospora cubensis*), Alternaria sooty spot of Chinese mustard (*Alternaria brassicicola*), rice blast (*Pyricularia oryzae*), etc.

10 Claims, No Drawings

PYRIMIDINE DERIVATIVES, PROCESS FOR PREPARING THE SAME AND AGRICULTURAL OR HORTICULTURAL FUNGICIDAL COMPOSITION CONTAINING THE SAME

This is a continuation of application Ser. No. 07/127,426, filed Dec. 2, 1987, now abandoned.

FIELD OF THE INVENTION

This invention relates to pyrimidine derivatives and their salts as well as an agricultural or horticultural fungicidal composition comprising the same as an active ingredient. This invention also relates to a process for preparing the pyrimidine derivatives.

BACKGROUND OF THE INVENTION

Many investigations on 2-anilinopyrimidine derivatives have heretofore been made, and some compounds are known to have activity chiefly in the field of fungicides. For instance, East German Patent No. 151,404 describes that 2-anilinopyrimidine derivatives represented by the general formula

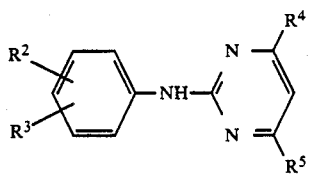

wherein $R^2$ and $R^3$ independently represent a hydrogen atom, an alkyl group which may be substituted, an aryl group, an aralkyl group, a halogen atom, a hydroxy group, an alkoxy group, an aryloxy group, a mercapto group, an alkylthio group, a carboxy group, an alkoxycarbonyl group, a carbamoyl group, a cyano group, a cyanato group, an isocyanato group, a thiocyanato group, an isothiocyanato group, a sulfo group, a halogenosulfonyl group, an amino group which may be substituted, a nitro group, or an acetyl group which may be substituted, and $R^4$ and $R^5$ represent a hydrogen atom or an alkyl group, have a fungicidal activity. Also, British Patent No. 1,245,085 discloses the fungicidal activity of pyrimidine derivatives represented by the general formula

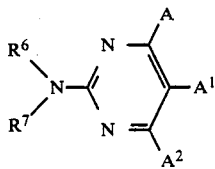

wherein A and $A^1$ represent a hydrogen atom, a nitro group, an amino group, a halogen atom, a hydrocarbon group or hydrocarbon groups which may be substituted, $R^6$ and $R^7$ represent a hydrogen atom or organic groups, and $A^2$ represents a halogen atom.

These conventional compounds are, however, found to have defects that their fungicidal activity is weak, and moreover their anti-microbial spectrum is narrow.

SUMMARY OF THE INVENTION

With view to developing a useful agricultural or horticultural fungicide, various pyrimidine have been synthesized and their physiological activities have been investigated. As the result, it has been discovered that the pyrimidine deivatives and their salts of this invention represented by the general formula (I)

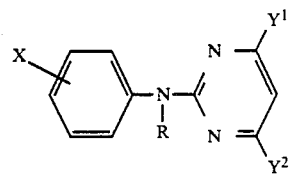

wherein X represents a hydrogen atom, a halogen atom, an alkyl group, an alkoxy group, a haloalkyl group or a cyano group; $Y^1$ represents an alkyl group, a cyanoalkyl group, an alkoxy group, an alkynyl group which may be substituted with a hydroxy group, an alkenyl group substituted with a hydroxy group and a halogen atom, a methylamino group, an alkoxyalkyloxy group, an alkylthioalkyl group or a group —$CH_2OR^1$ (where $R^1$ represents a hydrogen group, an alkyl group, an alkenyl group or an alkynyl group); $Y^2$ represents a halogen group, an alkyl group or a haloalkyl group; R represents a hydrogen atom, an alkyl group, a nitroso group, an alkoxyalkyl group, an alkoxyalkyloxyalkyl group, an alkenyl group, an alkynyl group, a formyl group or an alkylthioalkyl group; provided that (a) when $Y^1$ represents an alkynyl group or when $Y^1$ represents an alkoxy group and $Y^2$ represents a halogen atom or an alkyl group, X and R are not a hydrogen atom simultaneously, that (b) when $Y^1$ and $Y^2$ each represents an alkyl group, R is not a hydrogen atom, and that (c) when $Y^1$ represents an alkyl group and $Y^2$ represents a halogen atom, X and R are not a hydrogen atom simultaneously and X is not a halogen atom nor an alkyl group, have an excellent fungicidal activity for various plant pathogenic fungi, especially gray mold (*Botrytis cinerea*), and thus this invention has been accomplished.

DETAILED DESCRIPTION OF THE INVENTION

In the general formula (I), the halogen atom represented by X includes fluorine, chlorine, bromine and iodine. The alkyl group represented by X preferably contains 1 to 7 carbon atoms and includes a methyl group, and ethyl group, etc. The alkoxy group represented by X preferably contains 1 to 7 carbon atoms and includes a methoxy group, an ethoxy group, etc. The haloalkyl group represented by X preferably contains 1 to 7 carbon atoms and includes a trifluoromethyl group, etc.

The alkyl group represented by $Y^1$ preferably contains 1 to 7 carbon atoms and includes a methyl group, etc. The cyanoalkyl group represented by $Y^1$ preferably contains 1 to 7 carbon atoms and includes a cyanomethyl group, etc. The alkoxy group represented by $Y^1$ contains preferably 1 to 7 carbon atoms and includes a methoxy group, an ethoxy group, etc. The alkenyl group substituted with a hydroxy group and a halogen atom represented by $Y^1$ preferably contains 2 to 7 carbon atoms and includes a 2-chloro-3-hydroxpropen-1-yl group, etc. The alkynyl group which may be substituted with a hydroxy group represented by $Y^1$ preferably contains 2 to 7 carbon atoms and includes a propenyl-1-yl group, a 3-hydroxypropyn-1-yl group, etc. The alkoxyalkyloxy group represented by $Y^1$ preferably contains 2 to 7 carbon atoms and includes a methoxybutoxy group, an ethoxybutoxy group, etc. The alkylthioalkyl group represented by $Y^1$ preferably contains 2 to 7 carbon atoms and includes an ethylthiomethyl group, etc. The alkyl group represented by $R^1$ preferably contains 1 to 6 carbon atoms and includeds an ethyl group, a propyl group, etc. The alkenyl group represented by $R^1$ preferably contains 2 to 6 carbon atoms and includes a 2-propenyl group, etc. The alkynyl group represented by $R^1$ preferably contains 2 to 6 carbon atoms and includes a 2-propynyl group, etc.

The halogen atom represented by $Y^2$ includes fluorine, chlorine, bromine, iodine, etc. The alkyl group represented by $Y^2$ preferably contains 1 to 7 carbon atoms and includes a methyl group, etc. The haloalkyl represented by $Y^2$ preferably contains 1 to 7 carbon atoms and includes a fluoromethyl group, a chloromethyl group, a bromomethyl group, etc.

The alkyl group represented by R preferably contains 1 to 7 carbon atoms and includes a methyl group, etc. The alkoxyalkyl group represented by R preferably contains 2 to 7 carbon atoms and includes a methoxymethyl group, an ethoxymethyl group, a butoxymethyl group, etc. The alkoxyalkyloxyalkyl group represented by R preferably contains 3 to 10 carbon atoms and includes a methoxyethoxymethyl group, etc. The alkenyl group represented by R preferably contains 2 to 7 carbon atoms and includes a 2-propenyl group, etc. The alkynyl group represented by R preferably contains 2 to 7 carbon atoms and includes 2-propynyl group, etc. The alkylthioalkyl group represented by R preferably contains 2 to 7 carbon atoms and includes a methylthiomethyl group, etc.

However, in the above case, (a) when $Y^1$ represents an alkynyl group or when $Y^1$ represents an alkoxy group and $Y^2$ represents a halogen atom or an alkyl group, X and R are not a hydrogen atom simultaneously, (b) when $Y^1$ and $Y^2$ each represents an alkyl group, R is not a hydrogen atom, or (c) when $Y^1$ represents an alkyl group and $Y^2$ represents a halogen atom, X and R are not a hydrogen atom simultaneously, or X is not a halogen atom nor an alkyl group.

Preferably, $Y^1$ represents an alkyl group, an alkoxy group, an alkynyl group, a methylamino group or an alkoxyalkyl group. $Y^2$ preferably represents a halogen atom, an alkyl group or a haloalkyl group. R preferably represents a hydrogen atom, an alkoxyalkyl group or a formyl group. X preferably represents a hydrogen atom, a halogen atom or a cyano group. However, when $Y^1$ represents an alkynyl group or when $Y^1$ represents an alkoxy group and $Y^2$ represents a halogen atom or an alkyl group, X and R are not a hydrogen atom simultaneously. When $Y^1$ and $Y^2$ each represents an alkyl group, R is not a hydrogen atom. When $Y^1$ represents an alkyl group and $Y^2$ represents a halogen atom, X and R are not a hydrogen atom simultaneously and X is not a halogen atom.

More preferably, $Y^1$ represents an alkoxy group, an alkynyl group, a methylamino group or an alkoxyalkyl group, $Y^2$ represents a halogen atom, an alkyl group or a haloalkyl group, R represents a hydrogen atom, X represents a hydrogen atom, a halogen atom or a cyano group. However, when $Y^1$ represents an alkynyl group or when $Y^1$ represents an alkoxy group and $Y^2$ represents a halogen atom or an alkyl group, X is not a hydrogen atom.

Most preferably, $Y^1$ represents an alkyl group, an alkoxy group or an alkynyl group, $Y^2$ represents a halogen atom or an alkyl group, R represents a nitroso group, a formyl group, an alkxoyalkyl group or an alkoxyalkyloxyalkyl group, and X represents a hydrogen group.

Specific examples of the compounds of this invention represented by the above described general formula (I) are listed in Table 1 below. The numbers of the comdppounds are referred to in the subsequent description.

TABLE 1

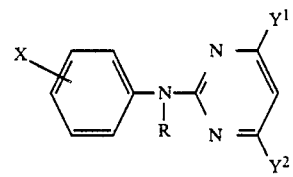

| COMPOUND | $Y^1$ | $Y^2$ | X | R | Melting Point (°C or Refractory Index $n_D^{20}$) |
|---|---|---|---|---|---|
| 1 | —OCH$_3$ | —CH$_2$Cl | H | H | 87–89 |
| 2 | —OCH$_3$ | —CH$_2$F | H | H | 78–80 |
| 3 | —CH$_2$OCH$_3$ | —CH$_3$ | H | H | 1.6010 |
| 4 | —CH$_2$OCH$_3$ | —Cl | H | H | 1.6353 |
| 5 | —OCH$_3$ | —CH$_3$ | 4-Cl | H | 101–103 |
| 6 | —CH$_3$ | —Cl | H | —CHO | 150–152 |
| 7 | —OCH$_3$ | —Cl | H | —CHO | 118–120 |
| 8 | —CH$_3$ | —CH$_3$ | H | —NO | 117–121 |
| 9 | —C≡CCH$_3$ | —CH$_3$ | 3-Cl | H | 128–130 |
| 10 | —C≡CCH$_3$ | —CH$_3$ | 4-Cl | H | 157–159 |
| 11 | —C≡CCH$_3$ | —CH$_3$ | 4-Br | H | 158–160 |
| 12 | —C≡CCH$_3$ | —CH$_3$ | 3-F | H | 127–129 |
| 13 | —C≡CCH$_3$ | —CH$_3$ | 4-F | H | 138.5–140 |
| 14 | —C≡CCH$_3$ | —CH$_3$ | H | —CHO | 147–148 |
| 15 | —C≡CCH$_3$ | —CH$_3$ | H | —CH$_2$OCH$_3$ | 1.5969 |
| 16 | —C≡CCH$_3$ | —CH$_3$ | H | —CH$_2$OC$_2$H$_5$ | 1.5882 |
| 17 | —C≡CCH$_3$ | —CH$_3$ | H | —CH$_2$OC$_2$H$_4$OCH$_3$ | 1.5790 |
| 18 | —C≡CCH$_3$ | —CH$_3$ | H | —CH$_2$OH═CH$_2$ | 1.6117 |
| 19 | —C≡CCH$_3$ | —CH$_3$ | H | —CH$_2$C≡CH | 1.6100 |
| 20 | —CH$_3$ | —CH$_3$ | H | —CHO | 138–139 |
| 21 | —CH$_3$ | —CH$_3$ | H | —CH$_2$C≡CH | 1.5885 |
| 22 | —CH$_3$ | —CH$_2$Cl | H | H | 100–101 |
| 23 | —CH$_3$ | —CH$_2$Br | H | H | 70–72 |
| 24 | —CH$_3$ | —Cl | H | CH$_3$ | 1.6051 |

TABLE 1-continued

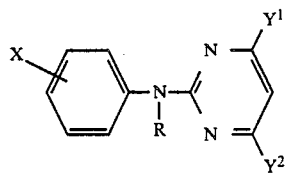

| COMPOUND | Y¹ | Y² | X | R | Melting Point (°C or Refractory Index $n_D^{20}$) |
|---|---|---|---|---|---|
| 25 | —CH$_2$CN | —CH$_3$ | H | H | 117–118 |
| 26 | —NHCH$_3$ | —Cl | H | H | 113–116 |
| 27 | —CH$_2$OH | —CH$_3$ | H | H | 118–120 |
| 28 | —CH$_2$OC$_2$H$_5$ | —CH$_3$ | H | H | 1.5924 |
| 29 | —C≡CCH$_3$ | —CH$_3$ | 4-I | H | 123–124 |
| 30 | —CH$_2$OC$_3$H$_7$-n | —CH$_3$ | H | H | 1.5846 |
| 31 | —CH$_2$OCH$_2$CH=CH$_2$ | —CH$_3$ | H | H | 1.6002 |
| 32 | —CH$_2$OCH$_2$C≡CH | —CH$_3$ | H | H | 1.6113 |
| 33 | —CH$_2$OC$_3$H$_7$-i | —CH$_3$ | H | H | 1.5771 |
| 34 | —C≡CCH$_3$ | —CH$_3$ | 4-CN | H | 171.5–172 |
| 35 | —C≡CCH$_2$OH | —CH$_3$ | H | H | 128–130 |
| 36 | —CH=C(Cl)CH$_2$OH | —CH$_3$ | H | H | 110–112 |
| 37 | —CH=C(Cl)CH$_2$OH | —CH$_3$ | H | H | 133–134.5 |
| 38 | —CH$_2$OC$_2$H$_5$ | —CH$_3$ | H | H | 1.5924 |
| 39 | —OC$_2$H$_4$OC$_2$H$_5$ | —CH$_3$ | H | H | 1.5868 |
| 40 | —OC$_2$H$_4$OCH$_3$ | —CH$_3$ | H | H | 1.5969 |
| 41 | —CH$_2$SC$_2$H$_5$ | —CH$_3$ | H | H | 1.6339 |
| 42 | —C≡CCH$_3$ | —CH$_3$ | 4-CF$_3$ | H | 136–138 |
| 43 | —OC$_2$H$_5$ | —CH$_3$ | 2-Cl | H | 42–43 |
| 44 | —OC$_2$H$_5$ | —CH$_3$ | 3-Cl | H | 98–100 |
| 45 | —OC$_2$H$_5$ | —CH$_3$ | 4-Cl | H | 91–93 |
| 46 | —OC$_2$H$_5$ | —CH$_3$ | 4-CH$_3$ | H | 77–78 |
| 47 | —OC$_2$H$_5$ | —CH$_3$ | 4-OCH$_3$ | H | 83–85 |
| 48 | —OC$_2$H$_5$ | —CH$_3$ | 2-CF$_3$ | H | 35–37 |
| 49 | —OC$_2$H$_5$ | —CH$_3$ | 3-CF$_3$ | H | 101–102 |
| 50 | —OC$_2$H$_5$ | —CH$_3$ | 4-CF$_3$ | H | 95–96 |
| 51 | —OC$_2$H$_5$ | —CH$_3$ | 4-F | H | 85–86 |
| 52 | —C≡CCH$_3$ | —CH$_3$ | 4-I | —CHO | 125–126.5 |
| 53 | —C≡CCH$_3$ | —CH$_3$ | H | —CH$_3$ | 1.6182 |
| 54 | —C≡CCH$_3$ | —CH$_3$ | H | —CH$_2$SCH$_3$ | 1.6260 |
| 55 | —CH$_3$ | —I | 4-CN | H | 184–186 |
| 56 | —C≡CCH$_3$ | —CH$_3$ | H | —CH$_2$OC$_4$H$_9$ | 1.5733 |

The compounds of this invention can be prepared in the following manner.

For example, the compounds of this invention represented by the general formula (I) in which R represents a formyl group or a hydrogen atom can be prepared by the following process.

Preparation Process 1

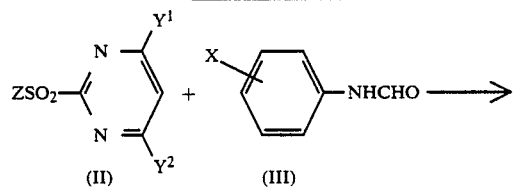

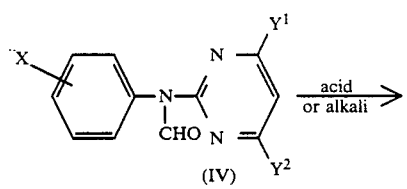

-continued
Preparation Process 1

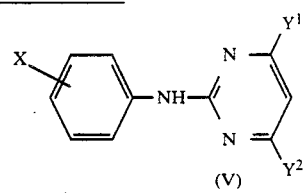

In the above formulae, Z represents an alkyl grpoup, a benzyl group or a substituted benzyl group, and Y¹, Y² and X have the same meanings as defined above.

The compound of the general formula (II) and the compound of the general formula (III) are reacted in a solvent (e.g., aromatic hydrocarbons such as benzene, toluene, xylene, etc., inert polar solvents such as dimethylformamide, dimethylacetamide, dimethylsulfoxide, etc., halogenated hydrocarbons such as dichloromethane, chloroform, carbon tetrachloride, etc., ethers such as diethyl ether, dioxane, tetrahydrofuran, etc., ketones such as acetone, methyl ethyl ketone, cyclohexanone, etc., nitriles such as acetonitrile, propionitriles, etc.) in the presence of a base (e.g., alkali metals, alkali metal hydrides, alkali metal hydroxides, etc.) at a reaction temperature of from −20° C to the boiling point of the solvent used, preferably from room temperature to 100° C, to form an N-formylated derivative of the general formula (IV). The compound (IV) is then hydrolyzed in a solvent, e.g., water or a mixed solvent composed of water and an organic solvent such as ethyl alcohol, etc. in the presence of an acid such as hydrochloric acid, hydrobromic acid, sulfuric acid, etc. or a base such as an alkali metal hydroxide, e.g., sodium hydroxide, potassium hydroxide, etc. at a temperature of from 0° C. to the boiling point of the solvent used, to form N-H form compound of the general formula (V). The thus-obtained compound (V) can be reacted with an acid (e.g, hydrochloric acid, sulfuric acid, nitric acid, etc.) to give salts thereof.

Of the compounds of this invention, those compounds represented by the general formula (I) in which R represents an alkyl group, an alkoxyalkyl group, an alkoxyalkyloxyalkyl group, an alkylthioalkyl group, an alkenyl group or an alkynyl group can be prepared by the following preparation process.

Preparation Process 2

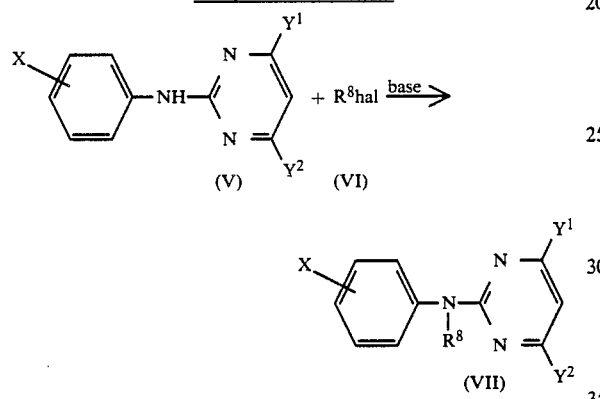

In the above formulae, hal represents a halogen atom, $R^8$ represents an alkyl group, an alkoxyalkyl group, an alkoxyalkyloxyalkyl group, an alkylthioalkyl group, an alkenyl group or an alkynyl group; $Y^1$, $Y^2$ and X have the same meanings as defined above.

In the above reaction, the compound of the general formula (V) and the compounds of the general formula (VI) are reacted in a solvent (e.g., aromatic hydrocarbons such as benzene, toluene, xylene, etc., inert polar solvents such as dimethylformamide, dimethylacetamide, dimethyl sulfoxide, etc., ethers such as dioxane, tetrahydrofuran, etc., ketones such as acetone, methyl ethyl ketone, cyclohexanone, etc., nitriles such as acetonitrile, propionitriles, etc.) in the presence of a base (e.g., alkali metals, alkali metal hydroxides, etc.) at a reaction temperature of from −20° C to the boiling point of the solvent used, preferably from room temperature to 100° C, to form compounds of this invention represented by the general formula (VII).

Of the compounds of this invention, those compounds of the general formula (I) in which R represents a nitroso group can be prepared by the following process.

Preparation Process 3

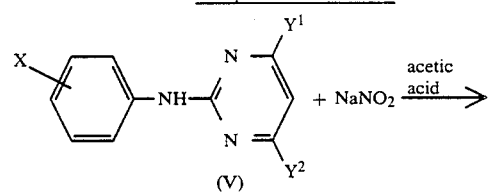

-continued
Preparation Process 3

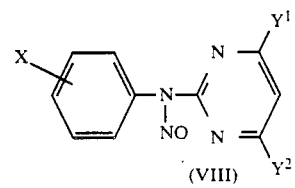

In the above formulae, $Y^1$, $Y^2$ and X have the same meanings as defined above.

In this reaction, the compound of the general formula (V) and sodium nitrite are reacted in acetic acid at room temperature to obtain compounds of the general formula (VIII).

Of the compounds of this invention represented by the general formula (I), those compounds in which R represents a hydrogen group, $Y^1$ represents an alkoxy group can be prepared by the following process.

Preparation Process 4

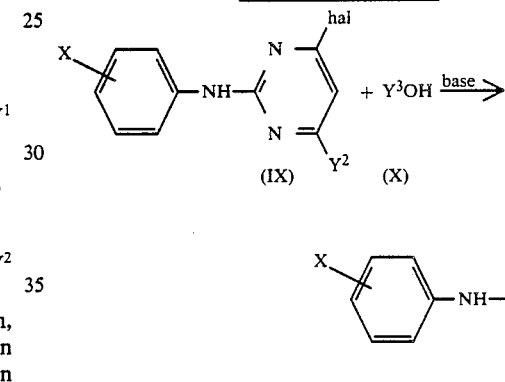

In the above formulae, $Y^3$ represents an alkyl group, and hal, $Y^2$ and X have the same meanings as defined above.

In the above reaction, the compound of the general formula (IX) and alcohol of the general formula (X) are reacted preferably in a solvent (e.g., those used in Preparation Process 1 above) or using an excessive amount of the alcohol of the general formula (X) so as to serve as a solvent, in the presence of a base (e.g., alkali metals, alkali metal hydroxides, carbonates and hydrides, etc.). The reaction is carried out at a reaction temperature of from −20° C to the boiling point of the solvent used, preferably from room temperature to 100° C, to obtain compounds of this invention represented by the general formula (XI).

Of the compounds of this invention represented by the general formula (I), those compounds in which R represents a hydrogen atom, $Y^1$ represents an alkoxyalkyl group and $Y^2$ represents an alkyl group can be prepared by the following process.

Preparation Process 5

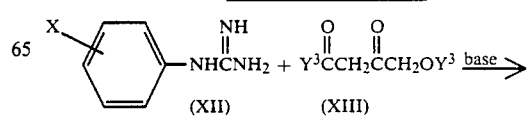

-continued
Preparation Process 5

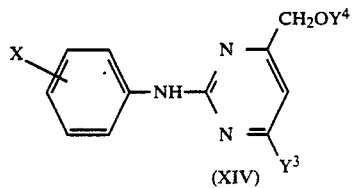

In the above formulae, $Y^4$ represents an alkyl group, and X and $Y^3$ have the same meanings as defined above.

In the above reaction, the compound of the general formula (XII) and the compound of the general formula (XIII) are reacted in a solvent (e.g., aromatic hydrocarbons such as benzene, toluene, xylene, etc., alcohols such as methanol, ethanol, etc., inert polar solvents such as dimethylformamide, dimethylacetamide, dimethyl sulfoxide, etc., ethers such as dioxane, tetrahydrofuran, etc.) in the presence of a base (e.g., alkali metals, alkali metal hydorxides, hydrides, carbonates, etc.) at a reaction temperature of from 0° C to the boiling point of the solvent used, to obtain compounds of this invention represented by the general formula (XIV).

Of the compounds of this invention represented by the general formula (I), those compounds in which R represents a hydrogen atom, $Y^1$ represents a halomethyl group or a group of the formula —$CH_2OR^1$ (where $R^1$ has the same meaning as defined above) and $Y^2$ represents an alkyl group can be prepared using the compound of the general formula (XIV) as a starting compound by the following process.

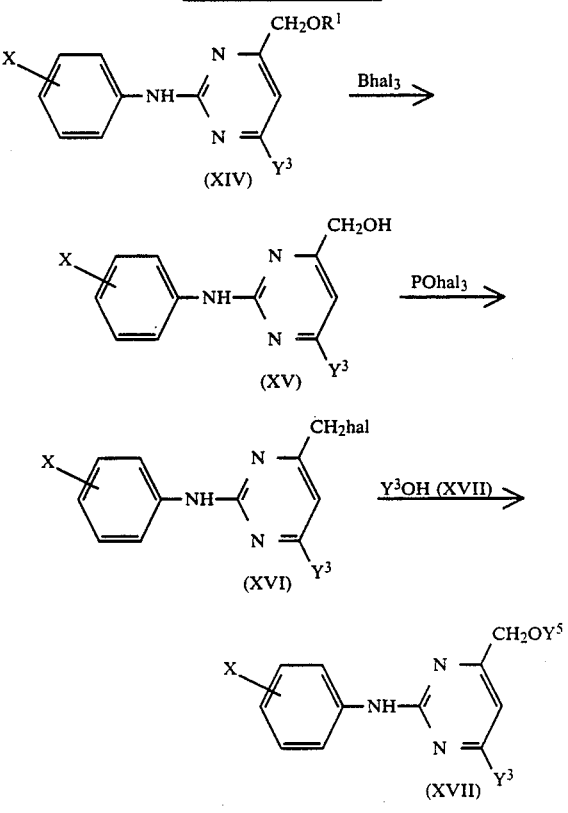

In the above formulae, $Y^5$ represents an alkyl group, an alkenyl group or an alkynyl group, and X, hal, $Y^3$ and $R^1$ have the same meanings as defined above.

In the above reaction, the compound of the general formula (XIV) and boron halide are reacted in a solvent such as dichloromethane, chloroform, benzene, etc. at a temperature of from −80° C to room temperature to obtain compounds of the general formula (XV). The compound of the general formula (XV) is further reacted with phosphorus oxyhalide or thionyl halide in a solvent (e.g., pyridine, benzene, chloroform, etc.) at a temperature of from −20° C to the boiling point of the solvent used to obtain compounds of the general formula (XVI). The compound of the general formula (XVI) is reacted with an alcohol preferably in a solvent (e.g., those solvents described in Preparation Process 1) or using an excess amount of the alcohol so as to serve as a solvent, in the presence of a base (e.g., alkali metals, hydroxides and hydrides of alkali metals, etc.) at a reaction temperature of from −20° C to the boiling point of the solvent used to obtain compounds of this invention represented by the general formula (XVII).

Now, with reference to concrete examples this invention will be explained in greater detail below.

EXAMPLE 1

Preparation of
2-(4-chloroanilino)-4-methoxy-6-methylpyrimidine
(Compound 5)

A 28% methanol solution of sodium methylate (1.5 g) was added to a solution of 1.5 g of 4-chloro-2-(4-chloroanilino)-6-methylpyrimidine in 50·ml of dimethylformamide and the mixture was stirred for 2 hours at 70° C After completion of the reaction, the reaction mixture was poured into water, extracted with 150 ml of toluene, washed with water, dried over Glauber's salt, and the toluene layer was concentrated by evaporation. The residue was purified by silica gel column chromatography to obtain 1.3 g (yield: 88%) of 2-(4-chloroanilino)-4-methoxy-6-methylpyrimidine having a melting point of 101°-103° C

EXAMPLE 2

Preparation of
4-chloro-2-(N-formylanilino)-6-methylpyrimidine
(Compound 6)

Formanilide (2.3 g) was added to a suspension in 50 ml of tetrahydrofuran of 0.9 g of sodium hydride (60%) of which oily component was removed with n-hexane, and the mixture was stirred at room temperature for 2 hours. To this was added 3.5 g of 4-chloro-6-methyl-2-methylsulfonylpyrimidine and the mixture was stirred at room temperature for 30 minutes. The reaction mixture was poured into water and extracted with ethyl acetate. The ethyl acetate layer was washed with water, dried over magnesium sulfate and concentrated by evaporation under reduced pressure. The residue was purified by silica gel column chromatography to obtain 2.0 g (yield: 48%) of 4-chloro-2-(N-formylanilino)-6-methylpyrimidine having a melting point of 150°-152° C.

EXAMPLE 3

Preparation of
2-(N-methoxymethylanilino)-4-methyl-6-(1-propynyl)-pyrimidine (Compound 15)

2-Anilino-4-methyl-6-(1-propynyl)pyrimidine (2.2 g) was added to a suspension in 50 ml of tetrahydrofuran of 0.5 g of sodium hydride (60%) of which oily component was removed with n-hexane, and the mixture was stirred for 30 minutes at 50°–55° C. After cooling to room temperature, 1.0 g of chloromethyl methyl ether was added to the mixture and stirred for 3 hours. The reaction mixture was poured into water and extracted with 150 ml of toluene. the toluene layer was washed with water, dried over Glauber's salt and concentrated by evaporation under reduced pressure. The residue was purified by silica gel column chromatography to obtain 1.7 g (yield: 63%) of 2-(N-methoxymethylanilino)-4-methyl-6-(1-propynyl)pyrimidine.
Refractive index: $n_D^{20}$ 1.5969.

EXAMPLE 4

Preparation of
2-(4-fluoroanilino)-4-methyl-6-(1-propynyl)-pyrimidine (Compound 13)

4-Fluoroformanilide (2.6 g) was added to a suspension in 100 ml of benzene of 0.8 g of sodium hydride (60%) of which oily component was removed with n-hexane, and the mixture was stirred under reflux for 30 minutes. After cooling to room temperature 4.0 g of 4-methyl-2-methylsulfonyl-6-(1-propynyl)pyrimidine was added. After stirring for 5 hours, the reaction mixture was washed with water. The benzene layer was dried over Glauber's salt and concentrated by evaporation under reduced pressure. The residue was dissolved in ethanol and 10 ml of a 10% aqueous sodium hydroxide solution was added to the solution, which was then stirred at room temperature for 2 hours. After addition of water, the reaction mixture was extracted with ethyl acetate. The ethyl acetate layer was dried over Glauber's salt and then concentrated by evaporation under reduced pressure. The residue was purified by silica gel column chromatography to obtain 3.0 g (yield: 63%) of 2-(4-fluoroanilino)-4-methyl-6-(1-propynyl)pyrimidine having a melting point of 138.5°–140° C.

EXAMPLE 5

Preparation of
4,6-dimethyl-2-(N-nitrosoanilino)pyrimidine (Compound 8)

To a solution of 2.0 g of 2-anilino-4,6-dimethylpyrimidine in 15 ml of acetic acid was added dropwise a solution of 1.4 g of sodium nitrite in 10 ml of water. After 30 minute's stirring, 50 ml of water was added to the mixture. The resulting crystals were collected by filtration and dried. Recrystallization from ethanol afforded 1.7 g (yield: 74%) of 4,6-dimethyl-2-(N-nitrosoanilino)-pyrimidine having a melting point of 117°–121° C.

EXAMPLE 6

Preparation of
2-anilino-4-methoxymethyl-6-methylpyrimidine (Compound 3)

A mixture of 4.5 g of phenylguanidine nitrate, 3.3 g of methoxyacetylacetone and 12 g of anhydrous sodium carbonate was heated with stirring and allowed to react at 150° C for 2 hours. After cooling to room temperature, water was added to the reaction mixture, which was then extracted with 150 ml of toluene. The toluene layer was washed with water, dried over Glauber's salt and concentrated by evaporation under reduced pressure. The residue was purified by silica gel column chromatography to obtain 3.5 g (yield: 68%) of 2-anilino-4-methoxymethyl-6-methylpyrimidine.
Refractive index $n_D^{20}$ 1.6010.

EXAMPLE 7

Preparation of
2-anilino-4-hydroxymethyl-6-methylpyrimidine (Compound 27)

Boron bromide (3.9 g) was added dropwise to a solution of 3.0 g of 2-anilino-4-methoxymethyl-6-methylpyrimidine in 100 ml of dichloromethane at −70° C After completion of the dropwise addition, the coolant was removed and the mixture was stirred at room temperature for 5 hours. The reaction mixture was poured into water gradually. The organic layer was washed with water, dried over magnesium sulfate and concentrated. The solid residue was recrystallized from ethanol-hexane to obtain 2.5 g (yield: 89%) of 2-anilino-4-hydroxymethyl-6-methyl-pyrimidine having a melting point of 118°–120° C.

EXAMPLE 8

Preparation of
2-anilino-4-chloromethyl-6-methylpyrimidine (Compound 22)

Phosphorus oxychloride (10 ml) was added to 1.5 g of 2-anilino-4-hydroxymethyl-6-methylpyrimidine and the mixture was heated under reflux for 15 minutes. After completion of the reaction, excessive phosphorus oxychloride was removed by distillation under reduced pressure. After dissolving the residue in dichloromethane, a 10% aqueous solution of sodium hydroxide was gradually added until the solution became alkaline under reflux of dichloromethane. After cooling to room temperature, the organic layer was washed with water, dried over magnesium sulfate and concentrated. The residual solid was recrystallized to obtain 1.2 g (yield: 73%) of 2-anilino-4-chloromethyl-6-methylpyrimidine having a melting point of 100°–101° C.

EXAMPLE 9

Preparation of
4-allyloxymethyl-2-anilino-6-methylpyrimidine (Compound 31)

Allyl alcohol (1.6 g) was added to a suspension in 40 ml of dimethylacetamide of 0.8 g of sodium hydride (60%) of which oily component was removed with n-hexane, and the mixture was stirred at 60° C for 1 hour. Then, after adding 2.2 g of 2-anilino-4-chloromethyl-6-methylpyrimidine, the mixture was further stirred at 60° C for 2 hours. The reaction mixture was poured into water, extracted with ethyl acetate, dried over magnesium sulfate and concentrated. The residue was purified by silica gel column chromatography to obtain 1.8 g (yield: 75%) of 4-allyloxymethyl-2-anilino-6-methylpyrimidine.
Refractive index $n_D^{20}$ 1.6002.

EXAMPLE 10

Preparation of
4-chloro-2-(-formylanilino)-6-methoxypryimidine
(Compound 7)

Formaniline (2.0 g) was added to a suspension in 50 ml of tetrahydrofuran of 0.7 g of sodium hydride (60%) of which oily component was removed with n-hexane, and the mixture was stirred under reflux for 1 hour. After cooling to room temperature, 5.0 g of 2-benzylsulfonyl-4-chloro-6-methoxypyrimidine was added to the mixture and the resulting mixture was stirred at room temperature for 1.5 hours. The reaction mixture was poured into water and extracted with 150 ml of ethyl acetate. The ethyl acetate layer was washed with water, dried over magnesium sulfate and concentrated by evaporation under reduced pressure. Recrystallization of the crude crystals thus-formed from benzene-hexane afforded 3.5 g (yield: 81%) of 4-chloro-2-(N-formylanilino)-6-methoxypyrimidine having a melting point of 118°–120° C.

EXAMPLE 11

Preparation of
2-(N-ethoxymethylanilino)-4-methyl-6-(1-propynyl)
pyrimidine (Compound 16)

A solution of 2-anilino-4-methyl-6-(1-propynyl)-pyrimidine (2.5 g) in dimethyl sulfoxide (2.5 ml) were added to a suspension in 50 ml of tetrahydrofuran of 0.5 g of sodium hydride (60%) of which oily component was removed, and the mixture was stirred at 50° C for 1 hour. After cooling to room temperature, 1.5 g of chloromethyl ethyl ether was added thereto and the resulting mixture was stirred for 5 hours. The reaction mixture was poured into water and extracted with 150 ml of toluene. The toluene layer was washed wit water, dried over magnesium sulfate and concentrated by evaporation under reduced pressure. The rsidue was purified by silica gel column chromatography to obtain 1.6 g (yield: 62%) of 2-(N-ethoxymethylanilino)-4-methyl-6-(1-propynyl) pyrimidine.

Refractive index: $n_D^{20}$ 1.5882.

EXAMPLE 12

Preparation of
2-(N-methoxyethoxymethylanilino)-4-methyl-6-(1-propynyl) pyrimidine (Compound 17)

A solution of 2-anilino-4-methyl-6-(1-propynyl)-pyrimidine (2.0 g) in dimethyl sulfoxide (2.5 ml) were added to a suspension in 50 ml of tetrahydrofuran of 0.4 g of sodium hydride (60%) of which oily component was removed, and the mixture was stirred at 50° C for 1 hour. After cooling to room temperature, 1.3 g of beta-methoxyethyoxy-methyl chloride was added thereto and the resulting mixture was stirred for 5 hours. The reaction mixture was poured into water and extracted with 150 ml of toluene. The toluene layer was washed with water, dried over magnesium sulfate and concentrated by evaporation under reduced pressure. The rsidue was purified by silica gel column chromatography to obtain 1.8 g (yield; 66%) of 2-(N-methoxyethoxymethylanilino)-4-methyl-6-(1-propynyl) pyrimidine.

Refractive index: $n_D^{20}$ 1.5790.

EXAMPLE 13

Preparation of
2-(N-formylanilino)-4,6-dimethylpyrimidine
(Compound 20)

Formanilide (2.2 g) was added to a suspension in 50 ml of tetrahydrofuran of 0.7 g of sodium hydride (60%) of which oily component was removed with n-hexane, and the mixture was sitrred at room temperature for 2 hours. 4,6-Dimethyl-2-methylsulfonylpyrimidine (3.5 g) was added to the mixture and the resulting mixture was stirred at room temperature for 1 hour. The reaction mixture was poured into water and extracted with 150 ml of ethyl acetate. The ethyl acetate layer was washed with water, dried over magnesium sulfate and concentrated by evaporation under reduced pressure. The residue was purified by silica gel column chromatography to obtain 2.0 g (yield: 49%) of 2-(N-formylanilino-4,6-dimethylpyrimidine having a melting point of 138°–139° C.

EXAMPLE 14

Preparation of
2-(N-butoxymethylanilino)-4-methyl-6-(1-propynyl)
pyrimidine (Compound 56)

A solution of 2-anilino-4-methyl-6-(1-propynyl)-pyrimidine (2.0 g) in dimethyl sulfoxide (2.5 ml) were added to a suspension in 50 ml of tetrahydrofuran of 0.4 g of sodium hydride (60%) of which oily component was removed, and the mixture was stirred at 50° C for 1 hour. After cooling to room temperature, 1.4 g of chloromethyl butyl ether was added thereto and the resulting mixture was stirred for 5 hours. The reaction mixture was poured into water and extracted with 150 ml of toluene. The toluene layer was washed with water, dried over magnesium sulfate and concentrated by evaporation under reduced pressure. The rsidue was purified by silica gel column chromatography to obtain 1.5 g (yield: 53%) of 2-(N-butoxymethylanilino)-4-methyl-6-(1-propynyl) pyrimidine.

Refractive index: $n_D^{20}$ 1.5733.

The agricultural or horticultural fungicide of this invention is a composition containing the pyrimidine derivative represented by the general formula (I) above or its salt as active ingredient. The compounds of this invention can be used as such. However, they usually are compounded with a carrier, a surface active agent, a dispersant, an adjuvant, etc. and then formulated by conventional methods into the form of dust, wettable powder, emulsifiable concentrate, fine grains, or granules. Examples of suitable carrier include, for instance, solid carriers such as talc, bentonite, clay, kaoline, diatomaceous earth, white carbon, vermiculite, slaked lime, silica sand, ammonium sulfate, urea, etc., and liquid carriers such as isopropyl alchohol, xylene, cyclohexanone, etc. Examples of surface active agent and dispersant include, for instance, sulfate esters of alcohol, alkylsulfonates, polyoxyethylene glycol ethers, polyoxyethylene alkyl aryl ethers, polyoxyethylene sorbitan monoalkylates, etc.

These preparations are diluted to a suitable concentration and sprayed, dusted or directly applied.

Usually, the fungicide of this invention can be applied in an amount of from about 1 g to about 100 kg per hectare, preferably 10 g to 10 kg per hectare. When it is sprayed to leaves and stems of plants it is usually diluted to a concentration of about 0.1 to about 10,000 ppm, preferably 100 to 3,000 ppm.

This invention will be described in greater detail with reference to the following formulation examples in which all percents are by weight.

EXAMPLE 15

Dust

Compound 5 (2%), 5% diatomaceous earth and 93% of clay were homogeneously mixed and pulverized to prepare a dust.

EXAMPLE 16

Wettable Powder

Compound 15 (50%), 45% of diatomaceous earth, 2% of sodium dinaphthylmethanedisulfonate, and 3% of sodium lignin sulfonate were homogeneously mixed and pulverized to prepare a wettable powder.

EXAMPLE 17

Emulsifiable Concentrate

Compound 3 (30%), 20% of cyclohexanone, 11% of polyoxyethylene alkyl aryl ether, 4% of calcium alkylbenzenesulfonate, and 35% of methylnaphthalene were homogeneously dissolved to prepare an emulsifiable concentrate.

EXAMPLE 18

Granules

Compound 16 (5%), 2% of sodium lauryl sulfate, 5% of sodium lignin sulfonate, 2% of carboxymethylcellulose, and 86% of clay were homogeneously mixed and pulverized. To the resulting mixture was added 20% of water, and the mixture was kneaded, processed into granular form of 14 to 32 mesh using an extruder type granulating machine and dried to prepare granules.

The agricltural or horticultural fungicidal composition of this invention possesses a broad antimicrobial spectrum showing an excellent activity against pathogenic fungi for crops or cultivated plants such as rice plant, wheat, barley, oats, rye, cucumber, Chinese mustard, apple, pear, grape, etc. The fungicide of this invention shows excellent activity as the controlling agents especially for rice blast (*Pyricularia oryzae*), cucumber downey mildew (*Pseudoperonospora cubensis*), cucumber gray mold (*Botrytis cinerea*), and Alternaria sooty spot of Chinese mustard (*Alternaria brassicicola*), and is also effective as the controlling agents for rice sheath blight (*Rhizoctonia solani*), cucumber anthracnose (*Colletotrichum lagenarium*), and apple Alternaria leaf spot (*Alternaria mali*).

The agricultural or horticultural fungicidal composition of this invention show high controlling activities for cucumber gray mold, cucumber down mildew, Alternaria sooty spot of Chinese mustard, rice blast, rice sheath blight, etc. even as compared with the compounds disclosed in the above-described East German Pat. No. 151,404 and British Pat. No. 1,245,085. Moreover, the agricultural or horticultural fungicidal composition of this invnetion are also characterized by that they are no harmful chemicals and yet excellent in the residual activity and persistence to rainfall, and not only the toxicity to warm-blooded animals but also the fish-toxicity is weak.

Among the agricultural or horticultural fungicidal composition of this invention, preferred are those which contain one or more of 2-(4-chloroanilino) -4-methoxy-6-methylpyrimidine, 4-chloro-2-(N-formylanilino)-6-methylpyrimidine, 2-(N-methoxymethylanilino)-4-methyl-6-(1-propynyl)pyrimidine, 2-(4-fluoroanilino)-4-methyl-6-(l-propynyl)pyrimidine, 4,6-dimethyl-2-(N-nitrosoanilino)-pyrimidine, 2-anilino-4-methoxymethyl-6-methylpyrimidine, 2-anilino-4-hydroxymethyl-6-methylpyrimidine, 2-anilino-4-chloromethyl-6-methyl-pyrimidine, 4-allyloxymethyl-2-anilino-6-methylpyrimidine, 4-chloro-2-(N-formylanilino)-6-methoxypyrimidine, 4-methyl-2-(N-ethoxymetylanilino)-6-(1-propynyl)-pyrimidine, 4-methyl-2-(N-methoxyethyloxymethylanilino)-6-(1-propynyl)pyrimidine, 4,6-dimethyl-2-(N-formylanilino)-pyrimidine, 4-methyl-2-(N-butoxymethylanilino)-6-(1-propynyl)pyrimidine, etc.

With reference to some test examples the effect achieved by the agricultural or horticultural fingicidal composition of this invention will be explained more concretely below.

TEST EXAMPLE 1

Test on the Effect of Controlling Cucumber Gray Mold

When the cucumber (variety: "Sagami hanjiro") which was grown by seeding in a population of 12 seeds per pot (square pot of 9 cm side) attained to the cotyledonous stage, a wettable powder prepared as in Example 16 was diluted to a 50 ppm with water, and sprayed with a spray gun in an amount of 5 ml per pot. After the air drying of the sprayed liquid, the plant was inoculated with a homogenized solution of the liquid cultured fungi of cucumber gray mold (*Botrytis cinerea*) by spraying. After three days of incubation in a moistured chamber, the number of the infected leaves was examined. The incidence of disease and controlling activity were caluculated according to the following standard. The results are shown in Table 2.

| Standard of Test | |
|---|---|
| Infection Index 0: | No lesion |
| Infection Index 1: | Infected area is less than ⅓ of leaf surface area |
| Infection Index 2: | Infected area is in the range of ⅓ to ⅔ of leaf surface area |
| Infection Index 3: | Infected area is more than ⅔ of leaf surface area |

$$\text{Incidence of Disease (\%)} = \frac{\Sigma \text{ (Infection Index} \times \text{Number of Leaves)}}{3 \times \text{Number of Examined Leaves}} \times 100$$

$$\text{Controlling Activity (\%)} = \frac{\text{Incidence of Disease in Treated Plot}}{\text{Incidence of Disease in Untreated Plot}} \times 100$$

were used for comparison.

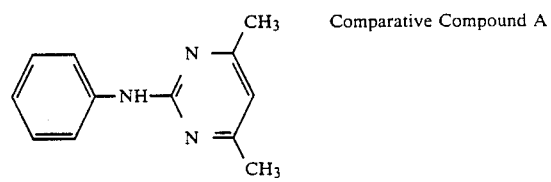

Comparative Compound A (Compound described in East German Patent 151,404)

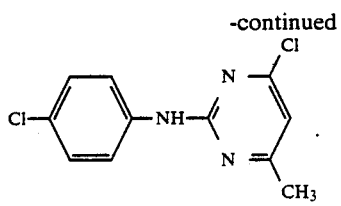

Comparative Compound B (Compound described in British Patent 1,245,085)

TABLE 2

| Compound Tested | Controlling Activity (%) |
| --- | --- |
| Compound 1 | 80.2 |
| Compound 2 | 100 |
| Compound 3 | 100 |
| Compound 4 | 83.3 |
| Compound 5 | 100 |
| Compound 6 | 100 |
| Compound 7 | 93.7 |
| Compound 8 | 99.3 |
| Compound 9 | 94.9 |
| Compound 10 | 98.3 |
| Compound 11 | 100 |
| Compound 12 | 100 |
| Compound 13 | 100 |
| Compound 15 | 99.1 |
| Compound 16 | 100 |
| Compound 17 | 100 |
| Compound 20 | 100 |
| Compound 26 | 100 |
| Compound 27 | 91.7 |
| Compound 34 | 100 |
| Compound 38 | 100 |
| Compound 56 | 100 |
| Comparative Compound A | 80.2 |
| Comparative Compound B | 35.9 |
| Untreated | 0 |

TEST EXAMPLE 2

Test on the Effect of Controlling Alternaria Sooty Spot of Chinese Mustard

When the Chinese mustard (variety: Okute Komatsuna) which was grown by seeding in a population of 15 seeds per pot (square pot of 9 cm side) attained to the cotyledonous stage, a wettable powder prepared as in Example 16 was diluted to 500 ppm with water, and sprayed in an amount of 5 ml per pot. After the air drying of the sprayed liquid, the plant was inoculated with fungi of Alternaria sooty spot (*Alternaria brassicicola*), which were cultured for one week or a PSA medium and the spore concentration was adjusted to 60 to 80 spores per visual field of a microscope (150 magnifications) by spraying. After the inoculation the plant was incubated for 3 days in a moistured chamber (30° C.), and the number of the leaf spots was counted, and the control activity was calculated from the average number of the spots per leaf according to the following equation.

Controlling Activity (%) =

$$\left(1 - \frac{\text{Average Number of Spots in Treated Plot}}{\text{Average Number of Spots in Untreated Plot}}\right) \times 100$$

The results are shown in Table 3.

TABLE 3

| Compound Tested | Controlling Activity (%) |
| --- | --- |
| Compound 2 | 86.8 |
| Compound 4 | 79.3 |
| Compound 8 | 88.8 |
| Compound 9 | 86.6 |
| Compound 10 | 73.2 |
| Compound 14 | 74 |
| Compound 15 | 73.6 |
| Compound 21 | 78.4 |
| Compound 22 | 83.9 |
| Compound 23 | 89.1 |
| Compound 25 | 95.7 |
| Compound 26 | 85.1 |
| Compound 28 | 100 |
| Compound 29 | 70.2 |
| Compound 30 | 100 |
| Compound 31 | 100 |
| Compound 32 | 100 |
| Compound 33 | 100 |
| Compound 35 | 97.2 |
| Compound 36 | 89.9 |
| Compound 37 | 91.6 |
| Compound 38 | 100 |
| Compound 39 | 98.3 |
| Compound 40 | 96.1 |
| Compound 41 | 90.6 |
| Compound 42 | 100 |
| Compound 45 | 84.7 |
| Compound 55 | 88.2 |
| Comparative Compound A | 0 |
| Untreated | 0 |

TEST EXAMPLE 3

Test on the Effect of Controlling Cucumber Downy Mildew

When the cucumber (variety: "Sagami hanjiro") which was grown by seeding in a population of 12 seeds per pot (square pot of 9 cm side) attained to the cotyledonous stage, a wettable powder prepared as in Example 16 was diluted to 500 ppm with water, and sprayed with a spray gun in an amount of 5 ml per pot. After the air drying of the sprayed liquid, the plant was inoculated with the fungi of cucumber downy mildew (*Pseudoperonospora cubensis*) whose spore concentration had been adjusted to 5 to 10 spores per visual field of a microscope (150 magnifications), by spraying. Twenty four (24) hours after the inoculation, the plant was allowed to be infected in a moistured chamber and then kept on a bench in a greenhouse. Seven days after the inoculation, the disease incidence was examined according to the following standard.

Healthy: No infection is discernible.
Slight: Infected area is less than $\frac{1}{3}$.
Moderate: Infected area is $\frac{1}{3}$ to $\frac{2}{3}$.
Severe: Infected area is more than $\frac{2}{3}$.

Incidence of Disease (%) =

$$\frac{(\text{Healthy} \times 0) + (\text{Slight} \times 1) + (\text{Moderate} \times 2) + (\text{Severe} \times 3)}{\text{Number of All Examined Leaves} \times 3} \times 100$$

Controlling Activity (%) =

$$\left(1 - \frac{\text{Incidence of Disease in Treated Plot}}{\text{Incidence of Disease in Untreated Plot}}\right) \times 100$$

The results obtained are shown in Table 4.

TABLE 4

| Compound Tested | Controlling Activity (%) |
|---|---|
| Compound 16 | 100 |
| Compound 23 | 91.7 |
| Compound 26 | 91.7 |
| Compound 41 | 83.3 |
| Compound 45 | 83.3 |
| Compound 47 | 91.7 |
| Compound 48 | 83.3 |
| Compound 50 | 83.3 |
| Compound 55 | 88.2 |
| Compound 56 | 100 |
| Comparative Compound A | 0 |
| Comparative Compound B | 0 |
| Untreated | 0 |

TEST EXAMPLE 4

Test on the Effect of Controlling Rice Blast

Twenty grains of rice seed (variety: Aichi asahi) were sowed in each white porcelain pot (diameter:9 cm) and grown for 3 to 4 weeks in a greenhouse. When the seedling developed 4th leaf, a wettable powder prepared as in Example 16 was diluted to 500 ppm with water, and sprayed with a spray gun in an amount of 10 ml per pot. After the air drying of the sprayed liquid, the plant was inoculated with a suspension of spores of rice blast (*Pyricularica oryzae*) by spraying and the pot was placed in a moistured chamber at 25° C. After five days from the inoculation the number of lesions was examined.

Controlling Activity (%) =

$$\left(1 - \frac{\text{Number of Lesion in Treated Plot}}{\text{Number of Lesions in Untreated Plot}}\right) \times 100$$

The results obtained are shown in Table 5.

TABLE 5

| Compound Tested | Controlling Activity (%) |
|---|---|
| Compound 1 | 95.7 |
| Compound 4 | 86.6 |
| Compound 8 | 94.4 |
| Compound 11 | 89.4 |
| Compound 12 | 78.2 |
| Compound 13 | 79.3 |
| Compound 14 | 80.1 |
| Compound 15 | 100 |
| Compound 16 | 74.9 |
| Compound 18 | 92.7 |
| Compound 23 | 82.3 |
| Compound 24 | 79.9 |
| Compound 25 | 75.1 |
| Compound 28 | 90.1 |
| Compound 30 | 97.5 |
| Compound 31 | 100 |
| Compound 32 | 99.5 |
| Compound 33 | 100 |
| Compound 38 | 90.1 |
| Compound 39 | 74.6 |
| Compound 41 | 99.5 |
| Compound 42 | 100 |
| Compound 48 | 88.5 |
| Compound 53 | 100 |
| Compound 54 | 94.6 |
| Compound 56 | 91.3 |
| Comparative Compound A | 0 |
| Untreated | 0 |

TEST EXAMPLE 5

Test on the Effect of Controlling Rice Sheath Blight

Fifteen (15) grains of rice (variety: Kinmaze) were showed in an unglazed pot diametre: (7 cm) and grown in a greenhouse for 4 to 5 weeks. When the seedling developed 5th leaf, a wettable powder prepared as in Example 16 was diluted to 500 ppm with water and sprayed in an amount of 10 ml per pot. After the air drying of the sprayed liquid, the plant was inoculated with the fungus of rice sheath blight (*Rhizoctonia solani*) cultured in a rice hulb bran medium for seven days on the foot of the plant and the pot was placed in a moistured chamber at 28° C. After five days from the inoculation, the height of the lesions formed on the leaf sheath of the plant was measured, and controlling activity was calculated according to the following equation.

Controlling Activity (%) =

$$\left(1 - \frac{\text{Height of Lesions in Treated Plot}}{\text{Height of Lesions in Untreated Plot}}\right) \times 100$$

The results obtained are shown in Table 6.

TABLE 6

| Compound Tested | Controlling Activity (%) |
|---|---|
| Compound 12 | 90.0 |
| Compound 15 | 97.1 |
| Compound 16 | 94.1 |
| Compound 17 | 93.5 |
| Compound 18 | 100 |
| Compound 19 | 94.8 |
| Compound 22 | 90.8 |
| Compound 26 | 83.8 |
| Compound 27 | 73.8 |
| Compound 28 | 93.5 |
| Compound 30 | 72.9 |
| Compound 33 | 75.7 |
| Compound 37 | 74.0 |
| Compound 38 | 93.5 |
| Compound 39 | 96.7 |
| Compound 40 | 97.6 |
| Compound 44 | 76.7 |
| Compound 45 | 85.0 |
| Compound 46 | 85.8 |
| Compound 47 | 72.5 |
| Compound 48 | 95.8 |
| Compound 49 | 92.4 |
| Compound 51 | 98.1 |
| Compound 52 | 100 |
| Compound 56 | 100 |
| Comparative Compound A | 25.2 |
| Untreated | 0 |

What is claimed:

1. A pyrimidine compound of formula (I):

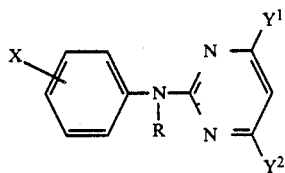

(I)

wherein X represents a hydrogen atom, a halogen atom, a lower alkyl group, a lower alkoxy group, a halo lower alkyl group or a cyano group; $Y^1$ represents a lower alkyl group, a cyano lower alkyl group, a lower alkoxy group, a lower alkenyl group substituted by a hydroxy group and a halogen atom, a lower alkynyl group which may be substituted by a hydroxy group, a methylamino group, a lower alkoxyalkyloxy group, a lower alkylthioalkyl group or a group of the formula —$CH_2OR^1$ where $R^1$ represents a hydrogen atom, a lower alkyl group, a lower alkenyl group or a lower alkynyl group; $Y^2$ represents a halogen atom, a lower alkyl group or a halo lower alkyl group; R represents a hydrogen atom, a lower alkyl group, a nitroso group, an alkoxy lower alkyl group, a lower alkoxyalkyloxyalkyl group, a lower alkenyl group, a lower alkynyl group, or a lower alkylthioalkyl group, with the proviso that (a) when $Y^1$ represents a lower alkynyl group or when $Y^1$ represents a lower alkoxy group and $Y^2$ represents a halogen atom or a lower alkyl group, X and R are not a hydrogen atom simultaneously, (b) when $Y^1$ and $Y^2$ each represents a lower alkyl group, R is not a hydrogen atom, or (c) when $Y^1$ represents a lower alkyl group and $Y^2$ represents a halogen atom, X and R are not a hydrogen atom simultaneously or X is not a halogen atom nor a lower alkyl group.

2. The pyrimidine compound as claimed in claim 1, wherein $Y^1$ represents a lower alkyl group, a lower alkoxy group, a lower alkynyl group, a methylamino group or a lower alkoxyalkyl group; $Y^2$ represents a halogen atom, a lower alkyl group or a halo lower alkyl group; R represents a hydrogen atom or a lower alkoxyalkyl group; and X represents a hydrogen atom, a halogen atom or a cyano group, with the proviso that when $Y^1$ represents a lower alkynyl group or when $Y^1$ represents a lower alkoxy group and $Y^2$ represents a halogen atom or a lower alkyl group, X and R are not a hydrogen atom simultaneously, that when $Y^1$ and $Y^2$ each represent a lower alkyl group, R is not a hydrogen atom, or that when $Y^1$ represents a lower alkyl group and $Y^2$ represents a halogen atom, X and R are not a hydrogen atom simultaneously and X is not a halogen atom.

3. A pyrimidine compound as claim in claim 1, wherein $Y^1$ represents a lower alkoxy group, a lower alkynyl group, a methylamino group or a lower alkoxyalkyl group; $Y^2$ represents a halogen atom, a lower alkyl group or a halo lower alkyl group; R represents a hydrogen atom; X represents a hydrogen atom, a halogen atom or a cyano group, with the proviso that when $Y^1$ represents a lower alkynyl group or when $Y^1$ represents a lower alkoxy group and $Y^2$ represents a halogen atom or a lower alkyl group, X is not a hydrogen atom.

4. The pyrimidine compound as claimed in claim 1, wherein $Y^1$ represents a lower alkyl group, a lower alkoxy group or a lower alkynyl group; $Y^2$ represents a halogen atom or a lower alkyl group; R represents a nitroso group, a lower alkoxyalkyl group or a lower alkoxyalkyloxyalkyl group; and X represents a hydrogen atom.

5. The pyrimidine compound as claimed in claim 1, wherein said lower alkyl and lower alkoxy groups each have 1 to 7 carbon atoms and said lower alkenyl and lower alkynyl groups each have 2 to 7 carbon atoms.

6. An agricultural or horticultural fungicidal composition comprising as an active ingredient a pyrimidine compound of formula (I):

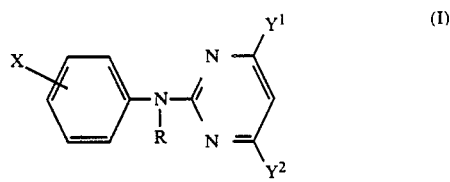

(I)

wherein X represents a hydrogen atom, a halogen atom, a lower alkyl group, a lower alkoxy group, a halo lower alkyl group or a cyano group; $Y^1$ represents a lower alkyl group, or a cyano lower alkyl group, a lower alkoxy group, a lower alkenyl group substituted with a hydroxy group and a halogen atom, a lower alkynyl group which may be substituted with a hydroxy group, a methylamino group, a lower alkoxyalkyloxy group, a lower alkylthioalkyl group or a group of the formula —$CH_2OR^1$ where $R^1$ represents a hydrogen atom, a lower alkyl group, a lower alkenyl group or a lower alkynyl group; $Y^2$ represents a halogen atom, a lower alkyl group or a halo lower alkyl group; R represents a hydrogen atom, a lower alkyl group, a nitroso group, a lower alkoxyalkyl group, a lower alkoxyalkyloxyalkyl group, a lower alkenyl group, a lower alkynyl group, or a lower alkylthioalkyl group, with the proviso that (a) when $Y^1$ represents an lower alkynyl group or when $Y^1$ represents a lower alkoxy group and $Y^2$ represents a halogen atom or a lower alkyl group, X and R are not a hydrogen atom simultaneously, (b) when $Y^1$ and $Y^2$ each represents a lower alkyl group, R is not a hydrogen atom, or (c) when $Y^1$ represents a lower alkyl group and $Y^2$ represents a halogen atom, X and R are not a hydrogen atom simultaneously or X is not a halogen atom nor a lower alkyl group.

7. The agricultural or horticultural fungicidal composition as claimed in claim 6, wherein $Y^1$ represents a lower alkyl group, a lower alkoxy group, a lower alkynyl group, a methylamino group or a lower alkoxyalkyl group; $Y^2$ represents a halogen atom, a lower alkyl group or a halo lower alkyl group; R represents a hydrogen atom or a lower alkoxyalkyl group; and X represents a hydrogen atom, a halogen atom or a cyano group, with the proviso that when $Y^1$ represents a lower alkynyl group or when $Y^1$ represents a lower alkoxy group and $Y^2$ represents a halogen atom or a lower alkyl group, X and R are not a hydrogen atom simultaneously, that when $Y^1$ and $Y^2$ each represents a lower alkyl group, R is not a hydrogen atom, or that when $Y^1$ represents a lower alkyl group and $Y^2$ represents a halogen atom, X and R are not a hydrogen atom simultaneously and X is not a halogen atom.

8. The agricultural or horticultural fungicidal composition as claimed in claim 6, wherein $Y^1$ represents a lower alkoxy group, a lower alkynyl group, a methylamino group or a lower alkoxyalkyl group; $Y^2$ represents a halogen atom, a lower alkyl group or a halo lower alkyl group; R represents a hydrogen atom; X represents a hydrogen atom, a halogen atom or a cyano group, with the proviso that when $Y^1$ represents a lower alkynyl group or when $Y^1$ represents a lower alkoxy group and $Y^2$ represents a halogen atom or a lower alkyl group, X is not a hydrogen atom.

9. The agricultural or horticultural fungicidal composition as claimed in claim 6, wherein $Y^1$ represents a lower alkyl group, a lower alkoxy group or a lower alkynyl group; $Y^2$ represents a halogen atom or a lower alkyl group; R represents a nitroso group, a lower alkoxyalkyl group or a lower alkoxyalkyloxyalkyl group; and X represents a hydrogen atom.

10. The agricultural or horticultural fungicidal composition as claimed in claim 6, wherein said lower alkyl and lower alkoxy groups each have 1 to 7 carbon atoms and said lower alkenyl and lower alkynyl groups each have 2 to 7 carbon atoms.

* * * * *